United States Patent [19]

Miethe et al.

[11] Patent Number: 5,122,462

[45] Date of Patent: Jun. 16, 1992

[54] PROCESS FOR THE ENZYMATIC PREPARATION OF OPTICALLY-ACTIVE CYANOHYDRINS

[75] Inventors: Peter Miethe, Halle; Maria-Regina Kula, Niederzier-Hambach; Ingeborg M. Stuertz, Eschweiler; Christian Wandrey; Udo Kragl, both of Juelich, all of Fed. Rep. of Germany

[73] Assignee: Forschungszentrum Juelich GmbH, Juelich, Fed. Rep. of Germany

[21] Appl. No.: 670,437

[22] Filed: Mar. 18, 1991

[30] Foreign Application Priority Data

Mar. 16, 1990 [DE] Fed. Rep. of Germany ....... 4008411
Mar. 16, 1990 [DE] Fed. Rep. of Germany ....... 4008412
Sep. 10, 1990 [DE] Fed. Rep. of Germany ....... 4028689

[51] Int. Cl.$^5$ .................. C12P 13/00; C12N 11/14; C12N 11/02; C09K 19/02
[52] U.S. Cl. .................. 435/128; 435/182; 435/280
[58] Field of Search .................. 435/128, 280, 182

[56] References Cited

U.S. PATENT DOCUMENTS

| 4,764,467 | 8/1988 | Goertz et al. | 435/182 |
| 4,800,162 | 1/1989 | Matson | 435/180 |
| 5,008,192 | 4/1991 | Neidermeyer et al. | 435/128 |
| 5,017,476 | 5/1991 | Miethe et al. | 435/123 |

FOREIGN PATENT DOCUMENTS

| 326063 | 8/1989 | European Pat. Off. . |
| 340744 | 11/1989 | European Pat. Off. . |
| 1300111 | 4/1970 | Fed. Rep. of Germany . |

OTHER PUBLICATIONS

Effenberger et al., Agnew. Chem. 99:491, 1987, pp. 491–492.
H. Frank et al., J. Chromatogr., 146: 197–208, 1987, pp. 197–206.

*Primary Examiner*—Herbert J. Lilling
*Attorney, Agent, or Firm*—Foley & Lardner

[57] ABSTRACT

The preparation of optically-active cyanohydrins from the corresponding oxo compounds is disclosed. The reaction of the oxo compounds with hydrocyanic acid is carried out in an organic solvent in the presence of (R)- or (S)-oxynitrilase (4.1.2.10) and (4.1.2.11), respectively, being solubilized in a lyotropic liquid crystal. Compounds which upon hydrolysis produce increased pH values are excluded as surface active agents. Preferably, surface active agents, the organic solvent and an aqueous buffer solution with a pH of 3 to 6, are mixed together to obtain a liquid crystal/organic solvent two-phase system. The liquid crystal is preferably fixed on a porous support, in particular a glass support. The reaction is carried out in a flow-through reactor which contains the liquid crystal in the abovementioned form or in thin layers adjacent to narrow flow channels, the borders of which are liquid permeable and through which the substrate-containing solvent is passed.

8 Claims, 1 Drawing Sheet

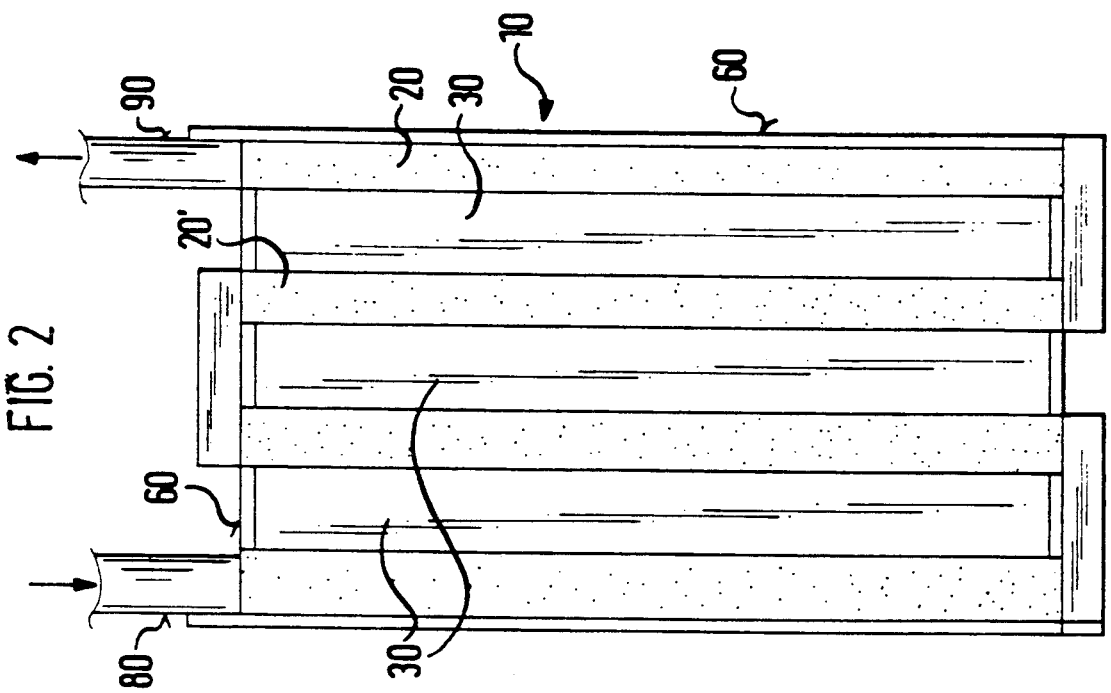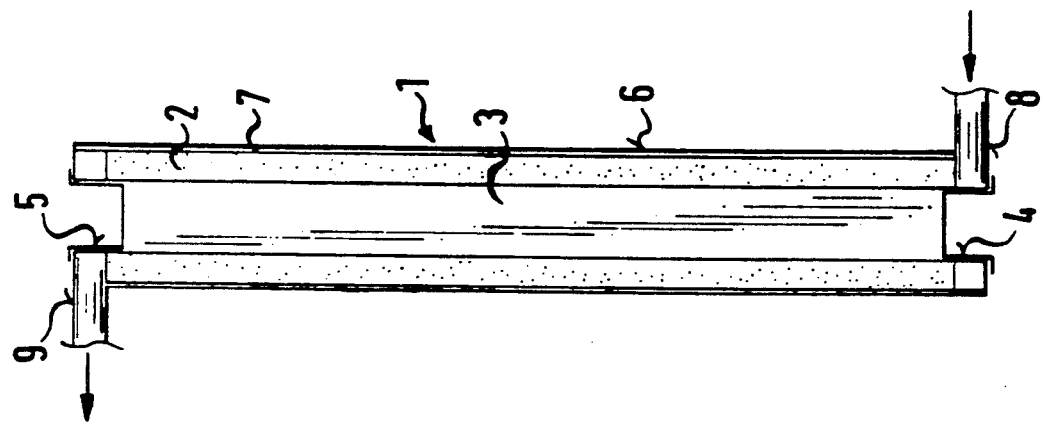

PROCESS FOR THE ENZYMATIC PREPARATION OF OPTICALLY-ACTIVE CYANOHYDRINS

BACKGROUND OF THE INVENTION

The present invention relates to a process for preparing optically-active cyanohydrins by enzymatic reaction of oxo compounds with hydrocyanic acid in the presence of (R)- or (S)-oxynitrilase (4.1.2.10) or (4.1.2.11), respectively, under conditions sufficiently acid for the competing chemical reaction which produces racemates to be negligible.

Optically-active cyanohydrins are of considerable interest for obtaining optically-active α-amino alcohols, α-hydroxy carboxylic acids, heterocycles and pyrethroid insecticides. Of central importance in this connection is the availability of chiral synthons that can be easily derivatized and that can be prepared at reasonable cost in adequate amounts with maximum enantiomer excess (ee).

In view of the optical selectivity of enzymatic reactions, the enzyme-catalyzed preparation of optically-active cyanohydrins has already been investigated. The optical purity of these compounds is a function of the efficiency of suppression of the competing chemical reaction.

German Patent 1,300,111 describes the preparation of optically-active cyanohydrins using (R)-oxynitrilase bound to ion exchangers at pH 5.4. However, the ee values achieved in the process were all below 90%.

Effenberger et al. (Anoew. Chem. 99:49 (1987)) therefore recommended the enzymatic reaction of oxo compounds with hydrocyanic acid in organic water-immiscible solvents in order to suppress the chemical reaction. A preferred process used enzyme immobilized on a support in ethyl acetate at pH values of 5.4. The ee values achieved were up to 99%. However, enzyme stability is lower in organic media.

Another way of suppressing the competing chemical reaction and racemization is disclosed in EP 326 063. According to this reference optically-active cyanohydrins are said to be obtained by reacting oxo compounds with hydrocyanic acid in the presence of oxynitrilase under conditions sufficiently acid, especially at pH values less than or equal to 4.5, and at such temperatures that the competing chemical reaction and racemization are negligible compared with the enzymatic synthesis. A low pH causes low enzyme activity. Increased losses in activity of the biocatalyst under these conditions are reported, and the examples reveal that low temperatures in the range from 5° to 8° C. are favored.

SUMMARY OF THE INVENTION

It is therefore an object of the present invention to provide a process for enzymatically preparing optically-active cyanohydrins which can be carried out at optimized conditions for the enzyme activity and stability while at the same time suppressing the competing chemical reaction which leads to the production of racemates. Such a process would provide both optimum yield and optimum optical purity.

It is a further object of the invention to provide a reactor for a reaction using a biocatalyst in the form of a lyotropic liquid crystal, in particular a reaction using an oxynitrilase to produce an optically-active cyanohydrin.

These and other objects according to the invention are provided by a process for preparing optically-active cyanohydrins, comprising the steps of solubilizing an oxynitrilase selecting from the group consisting of (R)-oxynitrilase (4.1.2.10) and (S)-oxynitrilase (4.1.2.11) in a lyotropic liquid crystal, where surfactants which produce an increase in pH upon hydrolysis are excluded from the liquid crystal formation; and enzymatically reacting an oxo compound with hydrocyanic acid in an organic solvent in the presence of the oxynitrilase solubilized in the lyotropic liquid crystal under conditions sufficiently acid for the competing chemical reaction and the racemization to be negligible in the defined reaction system.

The present invention also provides a flow-through reactor for a reaction using a biocatalyst in the form of a lyotropic liquid crystal, comprising a reactor housing; inlet and outlet distributors in the reactor housing; and at least one narrow flow channel in said reactor housing for a liquid containing a reactive substrate, the at least one flow channel being at least partially formed by selectively liquid-permeable layers of a porous material, the layers bordering on a layer containing a liquid crystal, the dimensions of which in a direction transverse to the direction of flow make possible an essentially complete penetration of the reactive substrate into the liquid crystal-containing layer.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows a reactor according to the present invention.

FIG. 2 shows a reactor according to the present invention comprising a series of plates.

DETAILED DESCRIPTION OF THE PREFERRED EMBODIMENTS

It has now been found, surprisingly, that the enzymatic synthesis can be preferred to the competing chemical reaction and racemizations in the acid range at pH values shifted towards the neutral point and at higher temperatures in comparison to aqueous systems when the biocatalyst is present in a form solubilized in a lyotropic liquid crystal, and the substrate is fed in via an organic solvent phase.

The process according to the invention comprises reaction in an organic solvent in the presence of oxynitrilase which has been solubilized in a lyotropic liquid crystal, where those surfactants whose hydrolysis results in an increase in the pH are ruled out for the liquid crystal formation. The oxo compound is contained in the organic phase, while the enzyme is present in the aqueous medium within the liquid crystal phase. In this way, a higher activity and stability are achieved than is possible with the purely organic media according to Effenberger et al. This optimum result relative to both yield and optical purity is achieved with pH values closer to the neutral point and without requiring low temperatures, both of which adversely affect enzyme stability and/or activity.

It is possible in this way to obtain optically-active (R)-cyanohydrins and (S)-cyanohydrins by reacting aliphatic or aromatic or heteroaromatic aldehydes or ketones with hydrocyanic acid in the presence of the (R)- or (S)-oxynitrilase, respectively, immobilized in the lyotropic liquid crystal. The preferred buffer solution used to produce the liquid crystalline phase is one having a pH between about 3 and 6.

Preferred surfactants are cationic or nonionic amphiphiles such as alkyltrimethylammonium halides, alkylpyridinium halides, polyoxyethylene ethers, polyoxyethylene esters, polyoxyethylene sorbitan esters, alkylphenol polyethylene glycol ethers, corresponding polyoxypropylene derivatives or copolyoxyethylenepolyoxypropylene derivatives or corresponding surfactant mixtures, and expedient organic solvents are, in particular, methylene chloride, chloroform, tetrachloromethane, dibutyl ether, diisopropyl ether or toluene. In practice, dibutyl ether and Brij ®35 (polyoxyethylene monolauryl ether) supplied by Serva have proven very suitable.

The preparation of the liquid crystalline biocatalyst-containing system expediently starts from an about 1 to 30% by weight, preferably about 5 to 10% by weight, stock solution or suspension of a surfactant in an organic solvent. Subsequently added to this stock solution are about 1 to 30% by weight, in particular about 5 to 10% by weight, of aqueous biocatalyst-containing buffer solution. Brief shaking results in a biphasic liquid crystal/organic solvent system.

The exact composition of a system of this type can be readily determined in appropriate preliminary tests if it cannot be found in the literature on colloid chemistry (surfactant/organic solvent/water ternary phase diagrams).

The process according to the invention is particularly suitable for reacting water-insoluble oxo compounds. In cases where the oxo compound is not too polar, it can itself form the organic solvent.

The biocatalyst-containing lyotropic liquid crystals are preferably mixed with porous support materials, such as, for example, porous sintered glass bodies. In use, they are particularly expediently employed to pack a continuous-flow column.

Particularly favorable in terms of process technology is a continuous-flow reactor which has thin layers of the biocatalyst-containing liquid crystal adjacent to narrow flow channels for substrate-containing solvent.

The enzymatic reaction of organic compounds in the presence of lyotropic liquid crystals which contain enzyme and which preferably have a reverse phase structure has been described in EP 340 744. Based on this disclosure it was entirely unexpected, however, that it would be possible, in the preparation of optically-active cyanohydrins by enzymatic means, to shift the pH towards the optimum enzyme reaction range of about pH 7 by using lyotropic liquid crystals. This makes it possible to carry out a successful reaction under favorable conditions, especially without the need to employ the special low temperatures of the aqueous system, and with relatively low enzyme losses. Of course, the reaction according to the invention can also take place within a relatively wide temperature range from about −10° C. to 70° C.

Surprisingly, in the case of the oxynitrilase, besides liquid crystals with reverse phase structure which have been preferably used to date, it is also possible equivalently to use those with normal phase structure. This fact considerably simplifies the choice and extends the possibilities of preparing a liquid crystalline reaction system.

The invention is described by means of the following examples.

EXAMPLE 1

A stock solution of 10% by weight decaethylene glycol dodecyl ether in dibutyl ether was prepared. To five (5) ml of this solution were added 280 µl of an aqueous R-oxynitrilase solution (protein concentration 10 mg/ml, 50 mM citrate buffer pH=3.75). Brief shaking resulted in a liquid crystal containing the enzyme in equilibrium with pure dibutyl ether. The ratio of the two phases is about 1:1 by volume. Subsequently, 100 mg of benzaldehyde and 100 µl of hydrocyanic acid were added to this system, and the cyanohydrin synthesis which started was followed by polarimetry in dibutyl ether. After 50 minutes, the rotation was constant, and the reaction was stopped. The organic phase was then removed from the liquid crystal, and the solvent was stripped in a rotary evaporator.

Chemical yield: 115 mg (90% of theory)
Optical purity: 99% ee

The optical purity was determined as N,O-bis-(pentafluoropropionyl)-2-amino-1-phenylethanol derivative of R-mandelonitrile by capillary gas chromatography by the method of H. Frank et al. (J. Chromatogr. 146: 197–208 (1987)) on a chiral phase (FS-Chirasil-Val, 25 m×0.32 mm).

The derivatization was carried out as follows: 1–2 mg of mandelonitrile were reduced with 250 µl of a M diborane solution (in tetrahydrofuran) in dibutyl ether at room temperature in 30 minutes. After the excess diborane had been hydrolyzed with a few drops of ethanol, and the solvent had been stripped, the resulting amino alcohol was directly acylated with 20 µl of pentafluoropropionic anhydride in methylene chloride at room temperature in 15 minutes. Finally, excess anhydride was stripped off in a rotary evaporator, and the residue was taken up again in methylene chloride and analyzed by gas chromatography.

EXAMPLE 2

Phenoxybenzaldehyde (100 mg) was reacted as in Example 1. The reaction was complete after 90 minutes. The working up of the cyanohydrin and the determination of the optical purity were carried out as described in Example 1.

Chemical yield: 90 mg (87% of theory)
Optical purity: 99% ee

EXAMPLE 3

Fluorobenzaldehyde (100 mg) was reacted as in Example 1. The reaction was complete after 90 minutes. The working up was carried out in analogy to Example.

Chemical yield: 102 mg (83% of theory)
Optical purity: 76% ee

EXAMPLE 4

2-Methylcyclohexanone (100 mg) was reacted as in Example 1. The reaction was complete after about 120 minutes. Working up and analysis were carried out in analogy to Example 1.

Chemical yield: 111 mg (82% of theory)
Optical purity: 92% de

EXAMPLE 5

Continuous production of (R)-mandelonitrile in a fixed-bed reactor.

A solution of 10% by weight Brij®35 (SIGMA) in diisopropyl ether was prepared. Seven hundred (700) µl of an aqueous solution of (R)-oxynitrilase (protein concentration 10 mg/ml, citrate buffer pH=4) were added to 20 ml of this solution. Brief shaking resulted in about six grams of lyotropic liquid crystal in equilibrium with diisopropyl ether. Three grams of this liquid crystalline biocatalyst were packed into the interior of 10 Siran Raschig rings (internal diameter 5 mm, length 5 mm). These Siran rings were placed in a 25 ml chromatography column, the column outlet was connected to a pump with connected bubble trap and polarimetric flow cell, and the system was filled with 30 ml of diisopropyl ether. After the column inlet had been coupled to an ice-cooled receiver which contained a diisopropyl ether solution with 25 µl/ml benzaldehyde and 25 µl/ml HCN, the reaction in the continuous flow apparatus was started by switching on the pump. Steady state was reached after about 140 minutes. The apparatus was operated continuously for 2 days, no reduction in the rotation being noted.

Operating conditions:
Benzaldehyde: 250 mM
HCN: 1 M
Residence time: 80 min
Average conversion: 95%
Space-time yield: 550 g/(1 d)
Optical purity: 99% ee

EXAMPLE 6

Continuous production of (R)-mandelonitrile in a fixed-bed reactor with different residence times.
Description of experiment:
Mixture:
2.5 g of Brij®35
10 ml of dibutyl ether
3.5 ml of R-oxynitrilase in 50 mM citrate buffer pH 3.75 (110 U/ml; 385 U in the mixture)
70 g of glass beads
Substrate concentrations:
90 mM benzaldehyde
200 mM hydrocyanic acid
Temperature: 25° C.
Polarimeter: $\lambda = 436$ nm
Total reactor volume: 50 ml
Volume through which flow is possible: 7.0 ml A solution of 25% by weight Brij®35 (SIGMA) in dibutyl ether was prepared. To 10 ml of this solution were added 3.5 ml of an aqueous solution of (R)-oxynitrilase (protein concentration 10 mg/ml, citrate buffer pH 3.75). Brief shaking resulted in approximately 6 g of lyotropic liquid crystal in equilibrium with dibutyl ether. The liquid crystalline biocatalyst was mixed with 70 g of glass beads and placed in a 50 ml chromatography column. The column outlet was connected to a pump with connected bubble trap and polarimetric flow cell, and the system was filled with 50 ml of dibutyl ether. After the column inlet had been coupled to an ice-cooled receiver which contained a dibutyl ether solution with 90 mM benzaldehyde and 200 mM hydrocyanic acid, the reaction in the continuous flow apparatus was started by switching on the pump. Various residence times were set, waiting in each case until the steady state was reached. The apparatus was operated continuously for 3 days, scarcely any reduction in the rotation being noted. The volume through which flow was possible was used to calculate the residence time and the space-time yield.

The conversion and the rotation at 10 different residence times were determined.

| Flow ml/min | α deg | RT min | c[BA] mM | c[MN] mM | Conversion % | ST yield g/l.d | ee % |
|---|---|---|---|---|---|---|---|
| 0.1 | 0.262 | 70 | 2 | 83 | 98 | 226 | 96 |
| 0.2 | 0.262 | 35 | 2 | 83 | 98 | 452 | 96 |
| 0.4 | 0.263 | 17.5 | 2 | 83 | 98 | 905 | 96 |
| 0.8 | 0.232 | 9 | 10 | 75 | 88 | 1600 | 95 |
| 1.6 | 0.183 | 4.4 | 32 | 61 | 72 | 2650 | 93.5 |
| 2.0 | 0.153 | 3.5 | 42 | 48 | 56 | 2633 | 96.5 |
| 2.4 | 0.112 | 3 | 61 | 32 | 38 | 2064 | 94 |
| 3.2 | 0.080 | 2.2 | 69 | 25 | 30 | 2160 | n.d. |
| 4.0 | 0.068 | 1.75 | 67 | 21 | 26 | 2312 | n.d. |
| 4.8 | 0.054 | 1.6 | 73 | 17 | 20 | 2070 | n.d. |

BA = benzaldehyde
MN = mandelonitrile

As is evident from the above table, the formation of mandelonitrile can be optimized: the highest space-time yields with virtually undiminished enantiomeric purity were obtained with residence times between 3 and 4 minutes in the series of experiments carried out.

EXAMPLE 7

Enzyme stability

Forty (40) liquid crystalline systems containing (R)-oxynitrilase were prepared as in Example 1 and were placed in 5 ml test tubes with ground joint. The oxynitrilase was stored in this form at room temperature, and the activity of the enzyme was measured after one day in each case. For this, 100 µl of benzaldehyde and 100 µl of HCN were placed in each of these tubes, and the rotation was measured discontinuously after 10, 20 and 40 minutes. The increase in this rotation/time plot was used as a measure of the enzyme activity. A fall of about 3% per day was noted during the first 4 days. After this, no further loss in activity was noted over a period of 40 days, and the enzyme activity was about 80% of the initial activity. The loss of activity by oxynitrilase in citrate buffer at pH=3.75 and 20° C. is about 8% per day.

EXAMPLE 8

Synthesis at pH 4 to 6.5

The procedure was as described in Example 5, employing various aqueous enzyme-containing solutions at pH=4.0, 4.5, 5.0, 5.5, 6.0 and 6.5. After continuous operation for 24 hours, the optical purity of the mandelonitrile formed in each case was determined. The results obtained are compiled in the table which follows:

| pH | 3.0 | 4 | 5 | 6 | 7 |
|---|---|---|---|---|---|
| % ee | 96.4 | 97.2 | 92.7 | 89 | 88.1 |

EXAMPLE 9

The reaction was carried out in a 100 ml two-neck flask with KPG stirrer. In order to convert the reaction system into a stirrable form, in which it is possible, in particular, to prevent adhesion of the liquid crystal to the stirrer blades, the following variants were developed:

(a) Two (2) g of polyethylene glycol 20 dodecyl ether (Brij ®35) are mixed at 50° C. with 40 ml of dibutyl ether. This results in a stock solution of surfactant in dibutyl ether. After cooling to 35° C., 2.8 ml of enzyme solution (protein concentration 18 mg/ml) are added. Vigorous shaking results in about 2 ml of liquid crystal. To this are added 50 ml of non-porous glass beads (d = 2–4 mm).

(b) The procedure is that described under (a). However, in place of the non-porous glass beads, 40 ml of porous Siran glass beads (Schott, d = 0.2–0.6 mm, pores 120 μm) are added. The system is briefly evacuated to remove air bubbles. Uptake of the liquid crystal mass into the cavities of the porous glass is, where appropriate, promoted by subsequent application of pressure (e.g., 2 bar).

(c) The procedure is as described under (a). However, in place of non-porous glass beads, 50 ml of sea sand or 50 ml of cellulose powder (Avicell, FMC) or 50 ml of dry bead cellulose (Leipziger Arzneimittelwerk) are added.

(d) When porous materials, e.g., cellulose powder, bead cellulose, Siran glass, are used, the procedure can also be as follows: 3 ml of the enzyme solution are added to 10 g of the support material. This moist support material is then added to 40 ml of the stock solution of Brij ®35 in dibutyl ether described under (a). In this procedure, the water content can be varied in the range from 2.6 to 8 ml per mixture.

(e) Forty (40) g of Eupergit ®C 250 L (Röhm Pharma) are mixed with 200 ml of R-oxynitrilase solution (1.9 g/l; pH = 7.5) and left to stand at room temperature for 72 hours. It is then washed with distilled water, and the immobilizate is dried in vacuo at room temperature for 24 hours. Forty (40) g of immobilizate are then wetted with 6 ml of citrate buffer of pH 3.75 and subsequently dispersed in 50 ml of the stock solution described under (a). The water content of the system can be varied within the limits from 2 to 10 ml per mixture.

In all cases, a stirring speed of 150 rpm at room temperature was used. In each case, 20 ml of water-saturated dibutyl ether, 2 ml of benzaldehyde and 2 ml of hydrocyanic acid were added. After a reaction time of 12 hours, the conversion was determined by HPLC (column RP-18, mobile phase acetonitrile/citrate buffer pH = 4.2 = 30/70), and the ee value was determined as described in Example 1. The findings were as follows:
Variant (a) Conversion 90%; ee = 97.2%
Variant (b) Conversion 86%; ee = 96.0%
Variant (c) Sea sand: conversion 87%; ee = 92.7%
Variant (c) Avicell: conversion 75%; ee = 91.0%
Variant (c) Bead cellulose: conversion 78%; ee = 88%
Variant (d) Conversion 86%, ee = 81%
Variant (e) Conversion 56%, ee = 78.8%

A flow-through reactor is convenient for carrying out reactions with the aid of biocatalysts that are contained in lyotropic liquid crystals. In the reactor, liquid crystal-containing layers alternate with flow channels for the substrate-containing liquid, the channels being formed at least in part by a porous material defining the liquid crystal containing layers. The dimensions of the layers transverse to the flow channels make possible an essentially complete penetration of the entire liquid crystal containing layer by the reactive substrate. The flow channels are preferably formed by layers of liquid permeable sintered materials and preferably fill less than about 50%, in particular less than about 30% of the reactor volume.

The liquid crystal containing-layer is preferably formed by a mixture of liquid crystals containing a biocatalyst with a porous support material, specifically porous sintered glass, and preferably has a layer thickness of less than about 1 cm. The thickness of the flow channels preferably is less than about 0.5 cm.

Suitable layouts are shown in FIGS. 1 and 2. FIG. 1 shows reactor 1 containing porous tube 2 which contains a liquid crystal filling comprising a biocatalyst. Tube 2 is sealed on the frontal side by caps or plugs 4, 5. Tube 2 fits slidingly into sheathing tube 6, which forms the reactor jacket and a flow channel for liquid flow, the flow channel being defined by gap 7, together with the port volume of tube 2. The liquid flows though inlet distributor 8 and leaves the reactor through outlet distributor 9. The terminal closure and liquid distributor are not shown in detail.

FIG. 2 shows a schematic layout of a plate module reactor 10, formed by a series of plates 20, which may be traversed by a flow in the same direction or alternatingly (as diagrammed), and between which liquid crystal layers 30 are provided. A reactor of this type, consisting of a plurality of plates, may be formed in the simplest manner by a stack of mutually independent plates 20, the longitudinal edges of which are sealed and closed off by reactor wall 80. At least one frontal side of the reactor jacket comprises inlet and outlet distributors for a substrate-containing liquid. Liquid crystal layers are applied to one or both sides 20' of plates 20, the thickness of the layers determining the space between the plates. Spacers may optionally be used to maintain the spacing selected. The gaps created by the intermediate spaces are filled by liquid crystal-containing layers 30.

What is claimed is:

1. A process for preparing optically-active cyanohydrins, comprising the steps of:
   solubilizing an oxynitrilase selected from the group consisting of (R)-oxynitrilase (4.1.2.10) and (S)-oxynitrilase (4.1.2.11) in a lyotropic liquid crystal, where surfactants which produce an increase in pH upon hydrolysis are excluded from the liquid crystal formation, the oxynitrilase catalyzing the production of an optically-active cyanohydrin; and
   enzymatically reacting an oxo compound with hydrocyanic acid in an organic solvent in the presence of the oxynitrilase solubilized in the lyotropic liquid crystal under conditions sufficiently acid for the competing chemical reaction and the racemization to be negligible.

2. The process as claimed in claim 1, wherein the reaction is carried out in a ternary system of surfactant/organic solvent/aqueous buffer which has been prepared using buffer solutions with pH values between 3 and 6.

3. The process as claimed in claim 1, wherein the reaction is carried out in a continuous flow reactor with liquid crystal immobilized on a porous support.

4. The process as claimed in claim 1, wherein the reaction is carried out in a continuous-flow reactor which contains the liquid crystal in a thin layer adjacent to narrow flow channels which have a liquid-permeable boundary and through which a substrate-containing solvent or solvent mixture is passed flowing tangentially to the liquid crystal layer.

5. The process as claimed in claim 1, wherein the oxynitrilase is (R)-oxynitrilase (4.1.2.10).

6. The process as claimed in claim 1, wherein the oxynitrilase is (S)-oxynitrilase (4.1.2.11).

7. The process as claimed in claim 1, wherein the reaction is carried out in a non-continuous reactor.

8. The process as claimed in claim 1, wherein the oxynitrilase is solubilized in a lyotropic liquid crystal immobilized on a porous support.

* * * * *